United States Patent
Arnold (10) Patent No.: US 12,009,077 B2
(45) Date of Patent: Jun. 11, 2024

(54) APPARATUS AND METHODS FOR ASSESSING A READINESS OF A MEDICAL ENTITY FOR PROVIDING PEDIATRIC PATIENT CARE

(71) Applicant: AJA Medical Consulting LLC, Miami, FL (US)

(72) Inventor: Alana Jacqueline Arnold, Miami, FL (US)

( * ) Notice: Subject to any disclaimer, the term of this patent is extended or adjusted under 35 U.S.C. 154(b) by 0 days.

(21) Appl. No.: 17/885,113

(22) Filed: Aug. 10, 2022

(65) Prior Publication Data
US 2024/0055084 A1 Feb. 15, 2024

(51) Int. Cl.
G16H 10/60 (2018.01)
G16H 40/20 (2018.01)
G16H 50/20 (2018.01)

(52) U.S. Cl.
CPC ............ G16H 10/60 (2018.01); G16H 40/20 (2018.01); *G16H 50/20* (2018.01)

(58) Field of Classification Search
USPC .......................................................... 705/2
See application file for complete search history.

(56) References Cited

U.S. PATENT DOCUMENTS

| | | |
|---|---|---|
| 8,452,610 B2 | 5/2013 | Lipner et al. |
| 11,145,407 B1 | 10/2021 | Jesneck et al. |
| 2005/0055245 A1 | 3/2005 | Oster et al. |
| 2005/0108052 A1* | 5/2005 | Omaboe ............... G16H 40/20 705/2 |
| 2008/0059292 A1 | 3/2008 | Myers et al. |
| 2008/0262869 A1* | 10/2008 | Bronn ................... G16H 80/00 706/45 |
| 2012/0260313 A1 | 10/2012 | Gomez |
| 2013/0013523 A1 | 1/2013 | Herrera Campos |
| 2015/0006261 A1 | 1/2015 | Gutman et al. |
| 2015/0310176 A1* | 10/2015 | Chen ................... H04L 51/214 705/2 |
| 2015/0310749 A1 | 10/2015 | Sergott |
| 2016/0110523 A1* | 4/2016 | Francois ............... G16H 10/20 705/2 |
| 2021/0241137 A1* | 8/2021 | Jain ...................... G16H 10/20 |
| 2022/0165398 A1* | 5/2022 | Avila-Hernandez ... G16H 50/20 |

FOREIGN PATENT DOCUMENTS

WO 2018200692 11/2018

OTHER PUBLICATIONS

Wieczorek, S. M. (2015). An exploratory study of Physician/Patient electronic messaging within secured health portals (Order No. 28371693). Available from ProQuest Dissertations and Theses Professional. (2498609167). (Year: 2015).*
Microsoft, Use the Hospital Emergency Response mobile app, Aug. 23, 2021.
Jensen Hughes, Smartplan™ Software System, Dec. 7, 2021.

* cited by examiner

*Primary Examiner* — Christopher L Gilligan
*Assistant Examiner* — Bennett Stephen Erickson
(74) *Attorney, Agent, or Firm* — Caldwell Intellectual Property Law (57) ABSTRACT

Provided in this disclosure are an apparatus and corresponding methods for assessing a readiness of a medical entity to provide care to a pediatric patient. A patient profile, a current expertise status, and an optimal expertise criterion may be inputted into a computing device to determine a real-time and/or continuous competency assessment of a medical entity.

16 Claims, 4 Drawing Sheets

APPARATUS AND METHODS FOR ASSESSING A READINESS OF A MEDICAL ENTITY FOR PROVIDING PEDIATRIC PATIENT CARE

FIELD OF THE INVENTION

The present disclosure generally relates to the field of healthcare. In particular, the present invention is directed to an apparatus and methods for assessing readiness of a medical entity for providing pediatric patient care.

BACKGROUND

Often medical entities are unprepared to provide care for pediatric patients, especially in emergency situations. Most emergency rooms are well-suited to treat adults, but often lack the supplies, staff, or proper procedures to care for children.

SUMMARY OF THE DISCLOSURE

In an aspect, an apparatus for determining readiness of a medical entity for providing pediatric patient care is presented. The apparatus includes: a processor; and a memory device communicatively connected to the processor and configured to provide instructions to the processor configured the processor to: receive an current expertise status of a medical entity; retrieve an optimal expertise criterion; and determine a pediatric care competency assessment for the medical entity as a function of the pediatric patient profile, the expertise datum, and the optimal expertise criterion.

In another aspect, a method for determining emergency readiness of a health institution for treating pediatric patients is presented. The method including: receiving, by a processor of a computing device that is configured by instructions stored in a memory of the computing device, a pediatric patient profile; identifying, by the processor, an current expertise status of a medical entity; retrieving, by the processor, an optimal expertise criterion; determining, by the processor, a pediatric care competency assessment for the medical entity as a function of the pediatric patient profile, the expertise datum, and the optimal expertise criterion.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to an apparatus and corresponding methods of assessing a preparedness of a medical entity, such as a health care professional, for providing care to a pediatric patient (i.e. child). Often children are brought into medical institutions, yet the medical institutions are not prepared to provide care. Such medical institutions may not have medical staff that specialize in pediatric care or are not stocked with proper equipment for pediatric patient care, such as properly sized supplies and/or equipment. An apparatus and corresponding methods are provided in this disclosure to assess a capability of a medical entity to provide pediatric care and suggest compensative measures that a medical entity may use to provide proper health care to a pediatric patient.

In the following description, for the purposes of explanation, numerous specific details are set forth in order to provide a thorough understanding of the present invention. It will be apparent, however, that the present invention may be practiced without these specific details. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims.

Figure 1:
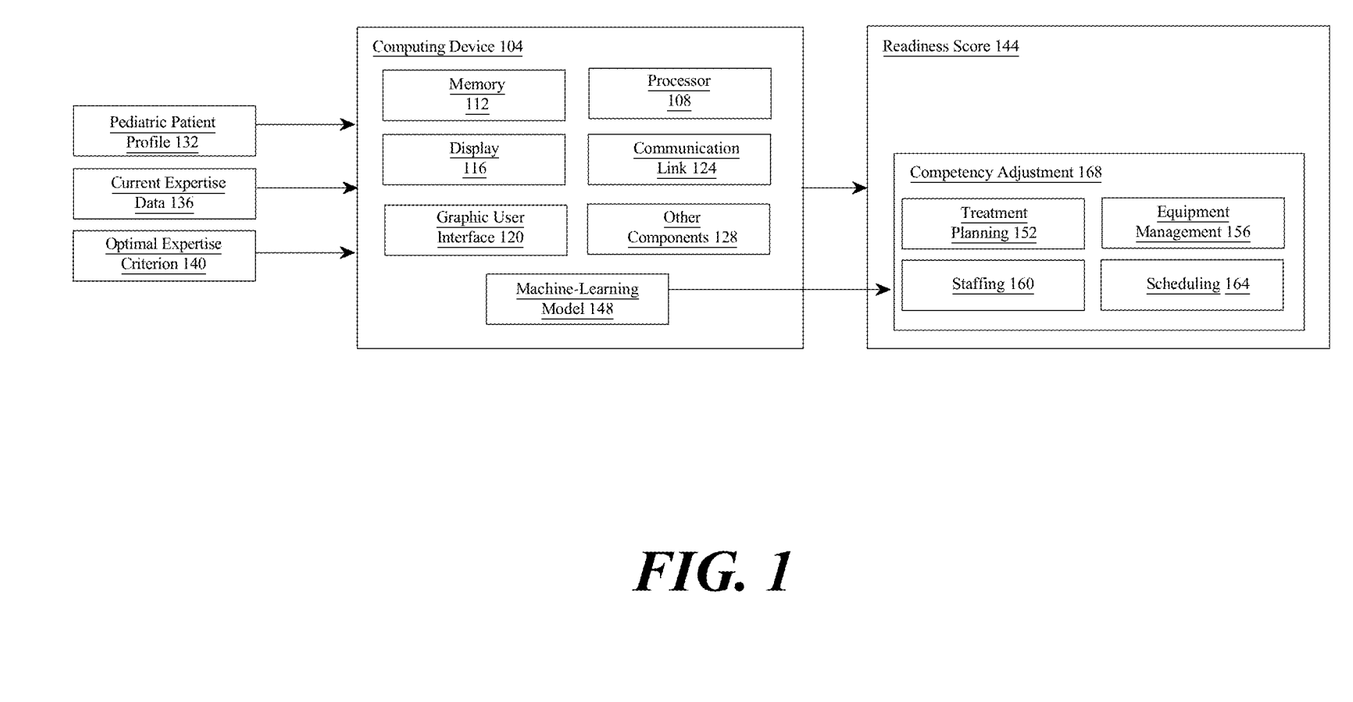
FIG. 1 is a block diagram illustrating an exemplary embodiment of an apparatus for determining readiness of a medical entity for providing pediatric patient care in accordance with one or more embodiments of the present disclosure.

Referring now to FIG. 1, an exemplary embodiment of an apparatus 100 for assessing readiness of a medical institution for pediatric patients is illustrated. Apparatus 100 includes a computing device 104. Computing device 104 may include any computing device as described in this disclosure, including without limitation a microcontroller, microprocessor, digital signal processor (DSP), a microcontroller, a processor, and/or system on a chip (SoC) as described in this disclosure. Computing device 104 may include a processor 108, a memory 112, a display 116, a graphic user interface 120, a communication link 124, and other components 128, such as a peripheral input device, sensor, and the like, as discussed further in this disclosure. Computing device 104 may include, be included in, and/or communicate with a mobile device such as a mobile telephone or smartphone, such as via communication link 124, which may be a wired or wireless communication. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device, such as communication link 124, may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of apparatus 100 and/or computing device 104. Non-limiting examples of computing device 104 may include an electronic book reading device, a computer workstation (e.g., a stationary computer workstation or a mobile computer workstation, such as a computer on wheels (COW), a terminal computer, a server computer, a handheld device (e.g., a tablet computer, a smartphone, and the like), a web appliance, a network router, a network switch, a network bridge, any machine capable of executing a sequence of instructions that specify an action to be taken by that machine, and any combinations thereof. In one example, a computing device may include and/or be included in a kiosk.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 may be configured to receive a pediatric patient profile 132. For the purposes of this disclosure, "pediatric patient profile" is a representation of information and/or data describing biological and/or health-related information associated with a pediatric patient. Pediatric patient profile may be associated with an individual or may be created by a user for proactive purposes. Pediatric patient profile 132 may include at least any of the following personal information: age, height, weight, heart rate, current diagnosis, medical history, allergies, current condition, current symptoms, known disorders, test results (e.g., basic metabolic panel, blood test, other physiological data, and the like), medications, growth chart, family history, and the like. For example, and without limitation, a pediatric profile may include information of a current condition such as a reported stomach pain of a pediatric patient. Pediatric patient profile 132 may be received by a user inputting pediatric information. For example, and without limitation, a guardian of the patient may manually input pediatric patient profile using a graphical user interface 120 of computing device 104 or a remote device, such as, for example, a smartphone or laptop owned by the guardian. In non-limiting embodiment, user may be prompted to input specific information or may fill out a questionnaire. Graphical user interface 120 may include without limitation, a form or other graphical element having display fields, where one or more elements of information may be displayed. For example, and without limitation, display 116 may show graphic user interface 120. Display 116 may include a touchscreen that a user may contact, such as using a hand or stylus pen, to interact with graphic user interface 120 to, for example, provide inputs, such as information related to pediatric patient profile 132. Information may also be inputted into graphical user interface 120 using other components 128, such as a peripheral input device, sensor, and the like. Graphical user interface 120 may include sliders that a user may adjust to indicate information of pediatric patient profile 132. In an embodiment, graphical user interface 120 may include free form textual entries, where a user may type in information regarding pediatric patient profile 132. In an embodiment, graphical user interface 120 may display a series of questions to prompt a user for information pertaining to pediatric patient profile 132. As a further example, computing device 104 may display a list of possible conditions to user, from which user may select each applicable condition the user currently suffers from. Computing device 104 may receive user selection of a user autoimmune disorders and select additional autoimmune disorders as a function of the user selection. In another example, and without limitation, a medical professional or personnel may input the pediatric patient profile 132 using graphic user interface of computing device 104 or a remote device. In another example, and without limitation, a third party, such as a different medical entity or healthcare provider, may transmit information of pediatric patient profile 132 to computing device 104. Pediatric patient profile 132 may be directly inputted into computing device 104. Pediatric patient profile 132 may be transmitted to computing device 104, such as via a wired or wireless communication, as previously discussed in this this disclosure.

In one or more embodiments, pediatric patient profile 132 may be stored in a memory 112 of computing device 104. Pediatric profile 108 may be stored in a database of memory 112 or of a third-party application that computing device 104 may access via, for example, a wired or wireless connection, to retrieve pediatric patient profile 132.

With continued referenced to FIG. 1, computing device 104 is configured to retrieve a current expertise status 136 of a medical entity. For the purposes of this disclosure, an "current expertise status" is a qualitative and/or quantitative representation associated with a current pediatric care capability of a medical entity. For the purposes of this disclosure, a "medical entity" is medical provider or institution that offers health services. A medical entity may include a person, such as a physician, an organization, a hospital, an office, an ambulance, and the like. For example, and without limitation, medical entity may refer to a physical location such as a medical building or room, or may include an organization, such as a managed care consortium and/or organization. For example, and without limitation, medical entity may include an emergency room or department of a medical institution. In another example, and without limitation, a medical entity may include a person, such as a dentist, nurse, physician, physical therapist, surgeon, and the like. A current pediatric care capability may include pediatric-trained staff, a rotation schedule for the pediatric-trained staff, a pediatric care protocol, necessary pediatric equipment, and the like. In a non-limiting embodiment, current expertise status 136 may include a quantitative value representing how many pediatric-trained staff members a medical entity has. In another non-limiting embodiment, current expertise status 136 includes whether or not a pediatric-trained staff, such as a pediatric nurse, is currently employed by the medical entity as well as the availability of the certain type of pediatric-trained staff. In another non-limiting embodiment, current expertise status 136 may include experience or training of medical staff and/or personnel. In another non-limiting embodiment, current expertise status 136 may include medical equipment and/or supply inventory. For example, current expertise status 16 may include whether or not a medical entity, such as a surgical room or an ambulance, is currently stocked with certain pediatric equipment. Pediatric equipment may include, but is not limited to, the following: general supplies, such as a patient warming device, an intravenous blood/fluid warmer, a restraint device, a weight scale, a tool or chart (e.g., Broselow tape) that uses weight and/or length to determine equipment size and correct drug dosing; monitoring supplies, such as blood pressure cuffs (e.g., neonatal, infant, child, adult sizes), an ECG monitor and/or defibrillator with pediatric and adult pads/paddles, a hypothermia thermometer, a pulse oximeter with pediatric and adult probes, a continuous end-tidal $CO_2$ monitoring device; Vascular Access supplies, such as an arm board (e.g., for an infant or child), an intravenous (IV) needle (e.g., 24 gauge and up), an intraosseous needle (e.g., for infant, child, or adult), an IV administration set with calibrated chambers and extension tubing and/or infusion devices with ability to regulate rate and volume of infusate, an umbilical vein catheter (e.g., 3.5F and 5.0F), a central venous catheter (e.g., 4.0F-7.0F); fracture-management supplies, such as a femur splint, a spine stabilization device; respiratory supplies, such as an endotracheal tube (e.g., 2.5 mm-8.0 mm (cuffed/uncuffed), a feeding tube (e.g., 5F, 8F), a laryngoscope blade (e.g., straight 0-3 and curved 2-3), a magill forcep, a nasopharyngeal airways (e.g., infant, child, adult), an oropharyngeal airway (e.g., size 0-5), a stylet for endotracheal tube, suction catheter (e.g., for an infant, child, and/or adult), a tracheostomy tube (e.g., 2.5, 3, 3.5, 4, 4.5, 5, 5.5 mm), a yankauer suction tip, a self-inflating resuscitator (e.g., an Ambu bag), a bag valve mask (BVM), masks for a self-inflating resuscitator (e.g., neonatal, infant, child, adult), clear oxygen masks (e.g., infant, child, adult), non-rebreather oxygen masks (e.g., infant, child, adult), nasal cannulas (e.g., infant, child, adult), basogastric tubes (e.g., infant (8F), child (10F), adult (14-18F), laryngeal mask airways (e.g., sizes 1, 1.5, 2, 2.5, 3, 4, 5); specialized trays and/or kits, such as a lumbar puncture tray (e.g., infant/pediatric 22G), supraglottic airways, laryngeal mask airways, cricothyrotomy supplies, surgical cricothyrotomy kit, tube thoracostomy tray, chest tubes (e.g., infant (10-12F), child (16-24F), adult (28-40F), newborn delivery kit, urinary catheterization kits and catheters (e.g., 6F-22F); dental tools, such as toothbrushes, bite wing tabs, short cup prophy angles, a replacement crown (e.g., size L64), molar band (e.g., pedo lower 23), and the like. In one or more embodiments, identifying current expertise status 136 may include a user manually inputting into computing device 104, such as via graphic user interface 120, by a user, such as medical entity or a representative of medical entity. In other embodiments, current expertise status 136 may be identified by computing device 136 or automatically populated by acquiring information from a database.

With continued reference to FIG. 1, computing device 104 is configured to obtain an optimal expertise criterion 140. Computing device 104 may retrieve optimal expertise criterion 140 from a database, a third-party application, medical entity, and the like. For the purposes of this disclosure, an "optimal expertise criterion" is information related to a desirable, recommended, or required pediatric care capability of a medical entity to care for a pediatric patient properly and/or be considered to have minimal readiness for a pediatric patient with a condition. In one or more embodiments, a recommended or required pediatric care capability may include minimal equipment requirements for pediatric care, certification necessary for pediatric-trained staff, type of pediatric-trained staff required for particular treatments or conditions of a pediatric patient, formal protocols that must be followed during pediatric care, necessary rotations of pediatric-trained staff during care of a pediatric patient, and the like. In a non-limiting embodiment, optimal expertise criterion 140 may include certification that a medical professional and/or personnel must have to be considered pediatric-trained staff. For example, and without limitation, a pediatric nurse must earn a pediatric nursing certification board (PNCB) certification from, for example, an accredited certification board to be considered a licensed and/or certified pediatric nurse practitioner, such as a Certified Pediatric Nurse (CPN), Acute Care Certified Pediatric Nurse Practitioner (CPNP-AC), Primary Care Certified Pediatric Nurse Practitioner (CPNP-PC), or Pediatric Primary Care Mental Health Specialist (PMHS). Pediatric-trained staff may include a nurse, physician, respiratory therapist (RT), hematologist, surgeon, physical therapist, dentist, dental assistant, or any other medical professional or personnel with knowledge and/or experience in healthcare related to children. In another non-limiting embodiment, optimal expertise criterion 140 may include standard protocols or treatment procedures related to specific pediatric patients and/or corresponding conditions. For example, and without limitation, a specific pediatric patient may include a ten-year-old female. In another example, and without limitation, a specific condition may include a fractured bone in an injured area and a proper protocol is requiring the patient to wear a cast for a predetermined amount of time on the injured area. Another example, and without limitation, a specific condition may include a cavity in a tooth where a proper protocol is removing the cavity and filling the tooth.

In one or more embodiments, optimal expertise criterion 140 may include evidence-based medicine and/or clinical protocols, such as protocols vetted by approved authorities and or provide by established literature. In other embodiments, optimal expertise criterion 140 may include nurse or staff training, where the nurse or staff training includes pediatric-specific knowledge. In other embodiments, optimal expertise criterion 140 may include physician training, where the physician training includes pediatric-specific knowledge. In other embodiments, optimal expertise criterion 140 may include simulation training, such as simulation training an emergency situation. In other embodiments, optimal expertise criterion 140 may include required or recommended pediatric equipment. In other embodiments, optimal expertise criterion 140 may include specialist accessibility, such as a medical entity having a respiratory therapist (RT) available that may administer breathing treatments. In other embodiments, optimal expertise criterion 140 may include interdepartmental management, such as established communication between adult ER staff and pediatric ER staff. In other embodiments, optimal expertise criterion 140 may include a transfer system, such as an EMS transport and/or ambulance that is stocked with pediatric equipment (e.g., advance life support). In other embodiments, optimal expertise criterion 140 may include having a pediatric point person, such as a head of pediatrics that communicates with non-pediatric staff or departments.

In one or more embodiments, optimal expertise criterion 140 may be retrieved from various sources. For example, and without limitation, optimal expertise criterion 140 may be retrieved from an accredited medical organization or department, medical journals, and the like. In one or more embodiments, computing device 104 may continuously monitor one or more databases, such as a plurality of databases, for current and/or updated optimal expertise criterion 140. For example, and without limitation, computing device 104 may retrieve updated optimal expertise criterion from a public database of a recognized authority. In another example, and without limitation, computing device 104 may retrieve updated optimal expertise criterion from a plurality of sources and/or databases to acquire a cumulation or collection of optimal expertise criteria. Computing device 104 may autonomously update optimal expertise criteria or may be instructed to retrieve updated optimal expertise criterion as a function of a user instruction using, for example, graphic user interface 120. A user, such as medical entity, may be able to view and or search through optimal expertise criterion 140 on display 116 using graphic user interface 120. Computing device 104 may provide information regarding the sources and/or citations associated with retrieved optimal expertise criterion 140. User may instruct computing device 104 which sources to retrieve optimal expertise criterion 140 from. User may instruct computing device 104 which sources to avoid retrieving optimal expertise criterion from. User may request computing device 140 retrieve specified optimal expertise criterion 140.

With continued reference to FIG. 1, computing device 104 is configured to identify a readiness score 144 of medical entity for patient care as a function of pediatric patient profile 132, current expertise status 244, and optimal expertise criterion 140. For the purposes of this disclosure, a "readiness score" is a qualitative or quantitative value representing a readiness of a medical entity to care for a pediatric patient with a particular condition. Thus, readiness score may be a qualitative and/or quantitative representation of whether or not a current pediatric care capability of a medical entity meets a recommended or required pediatric care standard for pediatric care under particular circumstances. Readiness score 144 may be a numerical value on a predetermined scale that ranks a readiness of medical entity. For example, a readiness score of a medical entity may be a numerical value, such as a 2 out of a scale of 10, for treating a pediatric patient with pneumonia. Readiness score 144 may be a score, such as a numerical value, that ranks a competency or capability of a medical entity associated with a certain category or in totality compared to an optimal expertise criterion and/or standard for that category or in totality.

In one or more embodiments, computing device 104 may determine a competency adjustment 168 as a function of readiness score 144. Computing device 104 may determine competency adjustment 168 using a machine-learning model 148, as discussed further in this disclosure. Competency adjustment 168 may be determine by comparing readiness score 144 to a preconfigured competency threshold and, if readiness score 144 is outside of preconfigured competency threshold, then competency adjustment 168 is suggested by computing device 104. For example, a preconfigured threshold may include a minimum readiness score necessary for a medical entity to be considered acceptably competent and ready to treat and/or care for a pediatric patient. For example, and without limitation, a readiness score of a medical entity may be a numerical value such as a 4 out of a scale of 10 for treating a pediatric patient with pneumonia. A competency threshold may include a minimum readiness score of a 6 out of 10 for a medical entity to be considered ready to treat a pediatric patient with pneumonia. Thus, the readiness score of the medical entity would be outside of the predetermined competency threshold and would not be considered competent enough to treat such a pediatric patient with pneumonia until a recommended competency adjustment is executed and/or completed. In response to readiness score 144 being outside of competency threshold, competency adjustment 168 is determined and recommended to medical entity so that, with the competency adjustment 168 a medical entity readiness score should fall within competency threshold after completing recommended competency adjustment. Referring back to the previous example, after a medical entity completes recommended competency adjustment 168, an updated readiness score of medical entity should fall within competency threshold, such as, for example, updated readiness score being an 8 out of 10 after completion of competency adjustment. Thus, an increase in readiness score occurs after completing competency adjustment 168. In one or more embodiments, if readiness score 144 exceeds preconfigured threshold by a predetermined maximum magnitude, then competency adjustment 168 may include transferring the pediatric patient to another medical entity, such as a second medical entity, that may properly treat pediatric patient. For example, and without limitation, a readiness score of a medical entity may be a numerical value such as a 2 out of a scale of 10 for treating a pediatric patient with pneumonia. A competency threshold may include a minimum readiness score of a 6 out of 10 for a medical entity to be considered ready to treat a pediatric patient with pneumonia. Thus, the readiness score of the medical entity would be outside of the predetermined competency threshold and would not be considered competent enough to treat such a pediatric patient with pneumonia until a recommended competency adjustment is executed and/or completed. Furthermore, a predetermined maximum magnitude may be considered a specific standard deviation from the preconfigured threshold, for example, a standard deviation of more than 3 outside of the preconfigured threshold, results in computing device 104 recommending transferring pediatric patient to a nearby second medical entity with a higher and acceptable readiness score. A competency adjustment 168 may still be provided to medical entity even if readiness score 144 exceeds maximum magnitude, so that medical entity may prepare for future pediatric patients with similar conditions.

A machine-learning module may be used to generate a threshold machine-learning model to determine competency threshold. Threshold machine-learning model may use determinations, classifications, and/or analysis steps, methods, processes, or the like. Threshold training data may contain correlations that a machine-learning process may use to model relationships between two or more categories of data elements. For instance, and without limitation, threshold training data may include a plurality of training data sets such as a first threshold training set, a second threshold training set, a third threshold training set, and so on. Multiple categories of data elements may be related in training data according to various correlations; correlations may indicate causative and/or predictive links between categories of data elements, which may be modeled as relationships such as mathematical relationships by machine-learning processes as described in further detail below. Threshold training data may include inputs, such as scientific data, that are correlated with outputs, such as preconfigured thresholds. Scientific data may include medical information, such as from medical texts, databases, studies, articles, inputted user data, past experience data, and the like. Scientific data may include information related to requirements or recommendations for treating and/or handling a particular condition of a pediatric patient. Outputs may include a minimum action needed to properly handle a condition of a pediatric patient. Various predetermined thresholds may be determined by threshold machine-learning model based on various types of situations and conditions. For example, and without limitation, a predetermined threshold may include a minimum equipment or tool requirement to operate in a pediatric patient. In another example, and without limitation, a predetermined threshold may include a minimum requirement of pediatric staff for triage in an emergency room.

In one or more embodiments, a machine-learning model may be used to determine readiness of a medical entity. For example, and without limitation, a readiness machine-learning model may be used to determine a readiness score of a medical entity. In one or more embodiments, the readiness scores may be weighted based on one or more factors, as discussed further below. In one or more embodiments, though readiness score 144 is within maximum magnitude, medical entity may still be recommended by computing device 104 via an alert to transfer pediatric patient to a second entity if a time to complete a competency adjustment 168 and/or increase a readiness score 144 to be within preconfigured threshold exceeds an allotted amount of time to care for a patient safely. For example, and without limitation, if a pediatric patient needs to be treated within an hour for appendicitis and a medical entity needs at least a day to complete competency adjustment 168, then computing device 104 will provide an alert that medical entity should transfer pediatric patient to a nearby second medical entity that can properly care for the pediatric patient within the allotted amount of time. In one or more embodiments, a machine-learning model may be used to calculate a recommendation score for one or more alternatives, or options, to competency adjustment 168. Thus, a plurality of competency scores may be ranked based on their assigned recommended scores. For example, and without limitation, a first competency adjustment may include contacting a second medical entity to acquire a piece of needed equipment, where the first competency adjustment has the highest recommendation score relative to the other recommended scores of the other competency adjustments. A second competency adjustment may include transferring the pediatric patient to a second medical entity that is already in possession of the needed equipment for treating the patient, where the second competency adjustment may have the second highest recommendation score. A third competency score may include contacting a local provider that medical entity may purchase the supply from, where the third competency score may have the third highest recommendation score. Any number of alternative competency adjustments with assigned recommendation scores may be recommended, as understood by one skilled in the art. Calculating a recommendation score may include taking into account various criteria, such as how long a competency adjustment will take, how long a medical entity has to treat a pediatric patient, a severity of the condition of the patient, mobility of patient, transportation of the medical entity, expense to medical entity and/or pediatric patient, and the like.

In some embodiments, a recommendation score of a competency adjustment may also be based on a competency adjustment and/or readiness score of one or more other medical entities. For example, and without limitation, a readiness score of a first medical entity may be 6 out of 10 at the current time, while the readiness score of a second entity may be 8 out of 10 at the current time. However, a machine-learning model may be trained to consider the readiness score at various times. For example, the readiness score of the second medical entity may be 4 out of 10 by the time the pediatric patient is transferred to the second entity because the criticalness of the condition of the pediatric patient will have increased within the time necessary to transfer the patient from the first medical entity to the second medical entity. Thus, a recommendation score for a competency adjustment may also be a function of a readiness score of a plurality of medical entities over time.

In one or more embodiments, computing device 104 may compute a recommendation score associated with each competency adjustment and select criteria to minimize and/or maximize the score, depending on whether an optimal result is represented, respectively, by a minimal and/or maximal score. A mathematical function, described herein as an "objective function," may be used by computing device 104 to score each possible pairing. Objective function may be based on one or more objectives. Computing device 104 may pair a predicted route, with a given courier, that optimizes objective function. In various embodiments, a score of a particular criterion may be based on a combination of one or more factors, including time, experience of medical entity, severity of condition, and the like. Each factor may be assigned a score based on predetermined variables. In some embodiments, the assigned scores may be weighted or unweighted. For example, and without limitation, time may be selected, such as by a user, to be a weighted factor that should hold the highest priority in determining recommended scores of various competency adjustments.

Optimization of objective function may include performing a greedy algorithm process. A "greedy algorithm" is defined as an algorithm that selects locally optimal choices, which may or may not generate a globally optimal solution. For instance, computing device 104 may select factors and/or criteria so that scores associated therewith are the best score for each competency adjustment and/or for each courier. In such an example, optimization may determine the combination of routes such that each delivery pairing includes the highest score possible.

In one or more embodiments, an objective function may be formulated as a linear objective function, which computing device 104 may solve using a linear program, such as and without limitation, a mixed-integer program. A "linear program," as used in this disclosure, is a program that optimizes a linear objective function, given at least a constraint. For instance, and without limitation, a constraint may include a time constraint. In various embodiments, computing device 104 may determine a factor that maximizes a total score subject to a constraint, such as time. A mathematical solver may be implemented to solve for the set of factors that maximize scores. Mathematical solver may be implemented on computing device 104 and/or another device mentioned in this disclosure, and/or may be implemented on third-party solver.

In one or more embodiments, optimizing objective function may include minimizing a loss function, where a "loss function" is an expression of an output of which an optimization algorithm minimizes to generate an optimal result. As a non-limiting example, and without limitation, computing device 104 may assign variables relating to a set of parameters, which may correspond to score components as described above, calculate an output of mathematical expression using the variables, and the like. Selection of different loss functions may result in identification of different potential pairings as generating minimal outputs.

In one or more embodiments, competency adjustment 168 may include recommendations for one or more categories to increase a readiness score for a particular category or in totality of a medical entity and thus provide medical entity with the proper elements for each area and/or category for providing proper pediatric patient care. Non-limiting examples of categories of competency adjustment may include treatment planning 152, equipment management 156, staffing 160, scheduling 164, and the like, as discussed above in this disclose in regard to optimal expertise criterion. In one or more embodiments, treatment planning 152 may include recommendations for providing treatments to a pediatric patient based on a condition and/or pediatric patient profile 132. In one or more embodiments, equipment management 156 may include recommending and assistance in acquiring proper medical equipment for pediatric patient care. In other embodiments, competency adjustment 168 may include computing device 104 providing information or autonomously contacting nearby medical entities that are in possession of necessary equipment or supplies that medical entity has been determined to need to provide proper care to a pediatric patient for a particular condition. For example, and without limitation, computing device 104 may provide contact information related to a neighboring hospital to medical entity that has, for example, required intubation equipment, such as a endotracheal tube (ETT), for a pediatric patient currently in the care of medical entity. Medical entity may then contact the neighboring hospital to acquire the intubation equipment. In one or more embodiments, competency adjustment 168 may include computing device 104 providing information regarding suppliers of medical devices that medical entity has been determined to need to provide proper care to a pediatric patient for a particular condition. In other embodiments, computing device 104 may automatedly contact one or more medical equipment suppliers to request and/or order needed medical equipment determined in competency adjustment 168. Computing device 104 may acquire information regarding local or remote medical equipment suppliers from a user input or database, such as, for example, a third-party web application. In one or more embodiments, staffing may include a type of pediatric healthcare professional required and/or or recommended for treating a pediatric patient with a specific condition and/or pediatric patient profile 132. Staffing 160 may also include providing training and or certification necessary for a healthcare professional to be considered a pediatric-trained staff member. In one or more embodiments, determining competency adjustment 104 includes providing training for medical staff. Competency adjustment 168 may include providing medical entity or staff required or recommended curriculum, such as training or certification curriculum. Curriculum may be provided by computing device, such as in the form of one or more learning modules, or curriculum may be provided by a third-party, such as a certification board, accredited program, or educational institution. For example, and without limitation, training for medical personnel may include recommending certification programs offered by a third party. In another example, and without limitation, training for medical personnel may also include offering a training program, such as a simulation, that allows medical personnel to learn a proper procedure or protocol to provide proper pediatric care to a patient, such as the patient described in a pediatric patient profile. In one or more embodiments, scheduling 164 may include computing device 104 providing rotations and/or scheduling for a plurality of pediatric-trained staff for a particular treatment plan of a pediatric patient.

Continuing in reference to FIG. 1, "training data," as used herein, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine learning processes as described in further detail below. In one or more embodiments, training data may include patient profile datum, expertise datum, and/or optimal expertise datum. As previously mentioned, training data may be acquired from a patient, medical entity, or third party, for instance via a questionnaire. In one or more exemplary embodiments, training data may be inputted using a remote device or a user interface of computing device 104, as previously discussed in this disclosure.

In one or more embodiments, computing device 104 may use a machine-learning model to determine competency adjustment 168. For example, and without limitation, computing device 104 may use competency machine-learning model 148 to obtain competency adjustment. A "competency machine-learning model" is a machine-learning model to produce a competency adjustment output given at least current expertise status 136 and optimal expertise criterion 140. This is in contrast to a non-machine learning software program where the commands to be executed are determined in advance by a user and written in a programming language. Competency machine-learning model 148 may include one or more competency machine-learning processes such as supervised, unsupervised, or reinforcement machine-learning processes that computing device 104 and/or a remote device may or may not use in the determination of competency adjustment 168. A competency machine-learning process may include, without limitation, machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

In one or more embodiments, computing device 104 may train and generate a competency machine-learning model as a function of pediatric patient profile 132, current expertise status 136, and/or optimal expertise criterion 140, wherein competency machine-learning model is trained by training data, wherein the training data contains a plurality of inputs (e.g., pediatric patient profiles, current expertise statuses, and/or optimal expertise criteria) correlated to a plurality of outputs (e.g., competency adjustments). For instance, and without limitation, training data may include pediatric patient profiles, current expertise statuses, and optimal expertise criteria as training data to train competency machine-learning model to "learn" based on a patient's physiological data, a medical entity's current capabilities, and/or a professional standard of capabilities. Competency machine-learning model may identify patterns in training data that then relates to, for instance and without limitation, inputted information and/or data that describe competency adjustment and categories thereof. In one or more embodiments, a second training data set with new and/or updated inputted information and corresponding correlations so that an updated competency machine-learning model may be generated by computing device 104.

In one or more embodiments, computing device 104 may receive competency machine-learning model 148 from a remote device that utilizes one or more competency machine-learning processes, wherein a remote device is described above in detail. For example, and without limitation, a remote device may include a computing device, external device, processor, and the like thereof. In one or more embodiments, a remote device may perform the competency machine-learning process using data to obtain a competency adjustment and transmit the output to computing device 104. In one or more embodiments, a remote device may transmit a signal, bit, datum, or parameter to computing device 104 that at least relates to a competency adjustment. Additionally or alternatively, a remote device may provide an updated machine-learning model. For example, and without limitation, an updated machine-learning model may be comprised of a firmware update, a software update, a competency machine-learning process correction, an updated competency machine-learning process, as described above, and the like thereof. Additionally or alternatively, the updated machine learning model may be transmitted to the remote device, wherein the remote device may replace the competency machine-learning model with the updated machine-learning model and obtain a competency adjustment as a function of inputted data using the updated machine-learning model. The updated machine-learning model may be transmitted by the remote device and received by computing device 104 as a software update, firmware update, or corrected baseline machine-learning model. For example, and without limitation competency machine-learning model may utilize a Naïve bayes machine-learning process, wherein the updated machine-learning model may incorporate decision tree machine-learning process. Additionally or alternatively, competency machine-learning model 116 may obtain a competency adjustment as a function of one or more classifiers.

Figure 2:
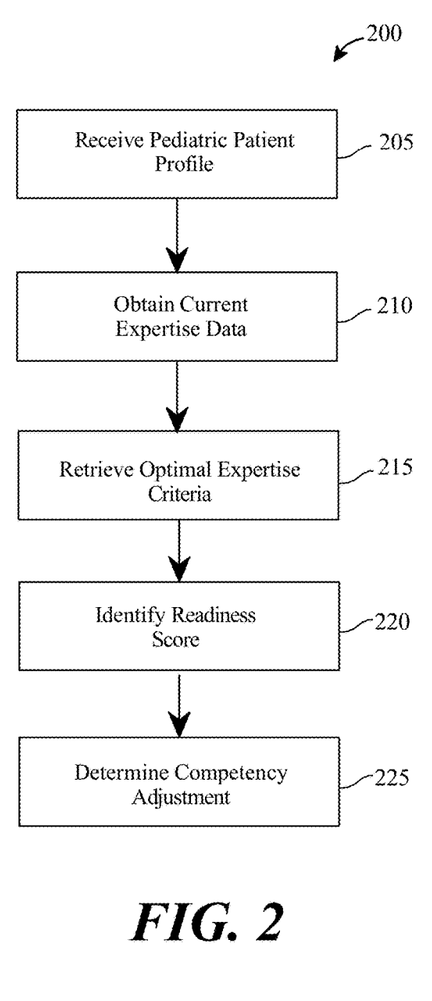
FIG. 2 is a flow diagram illustrating a method of determining readiness of a medical entity for providing pediatric patient care in accordance with one or more embodiments of the present disclosure.

Referring now to FIG. 2, a flowchart of an exemplary method 200 of determining a readiness of a medical entity for providing care to a pediatric patient. As shown in step 205, method 200 includes receiving, by processor of computing device that is configured by instructions stored in a memory of the computing device, pediatric patient profile. In one or more embodiments, pediatric patient profile includes a health condition of the pediatric patient. In one or more embodiments, pediatric patient profile comprises physiological datum of the pediatric patient. For the purposes of this disclosure, physiological data includes data and or characteristic of normal functions of the human body. Physiological data may include biophysical or biochemical processes, homeostatic control mechanisms, and communication between cells. Physiological data may include, for example and without limitation, blood content levels, such as white blood cell levels, sugar levels, and the like, muscle mechanics, homeostasis, organ function, a state of bones, and the like.

As shown in step 210, method 200 includes retrieving, by processor, a current expertise status of a medical entity. The current expertise status may include a medical equipment inventory, such as current supplies currently stocked by a medical entity. Medical equipment may be manually monitored and inventoried. In other embodiments, medical equipment and/or supplies may be inventoried by an automated system. Computing device 104 may include a present-time inventory list of medical equipment and/or supplies readily accessible to medical entity. In other or more embodiments, current expertise status includes access to an ambulance by medical entity. In other embodiments, current expertise status may include inventory of an ambulance. In one or more embodiments, current expertise status includes employed pediatric-trained staff.

As shown in step 215, method 200 includes obtaining, by processor, an optimal expertise criterion. In one or more embodiments, the optimal expertise criterion comprises qualifications of pediatric-trained staff.

As shown in step 220, method 200 includes identifying, by the processor, a readiness score for the medical entity as a function of the pediatric patient profile, the expertise datum, and the optimal expertise criterion.

As shown in step 225, method 200 includes determining competency adjustment as a function of readiness score. In one or more embodiments, determining the competency adjustment includes recommending a certification program for the medical entity. In one or more embodiments, determining the competency adjustment includes contacting a medical supplier or second medical entity, such as a neighboring medical entity, to acquire necessary medical equipment to properly care for the pediatric patient. In one or more embodiments, determining the competency adjustment includes providing a rotation schedule for the medical entity.

Figure 3:
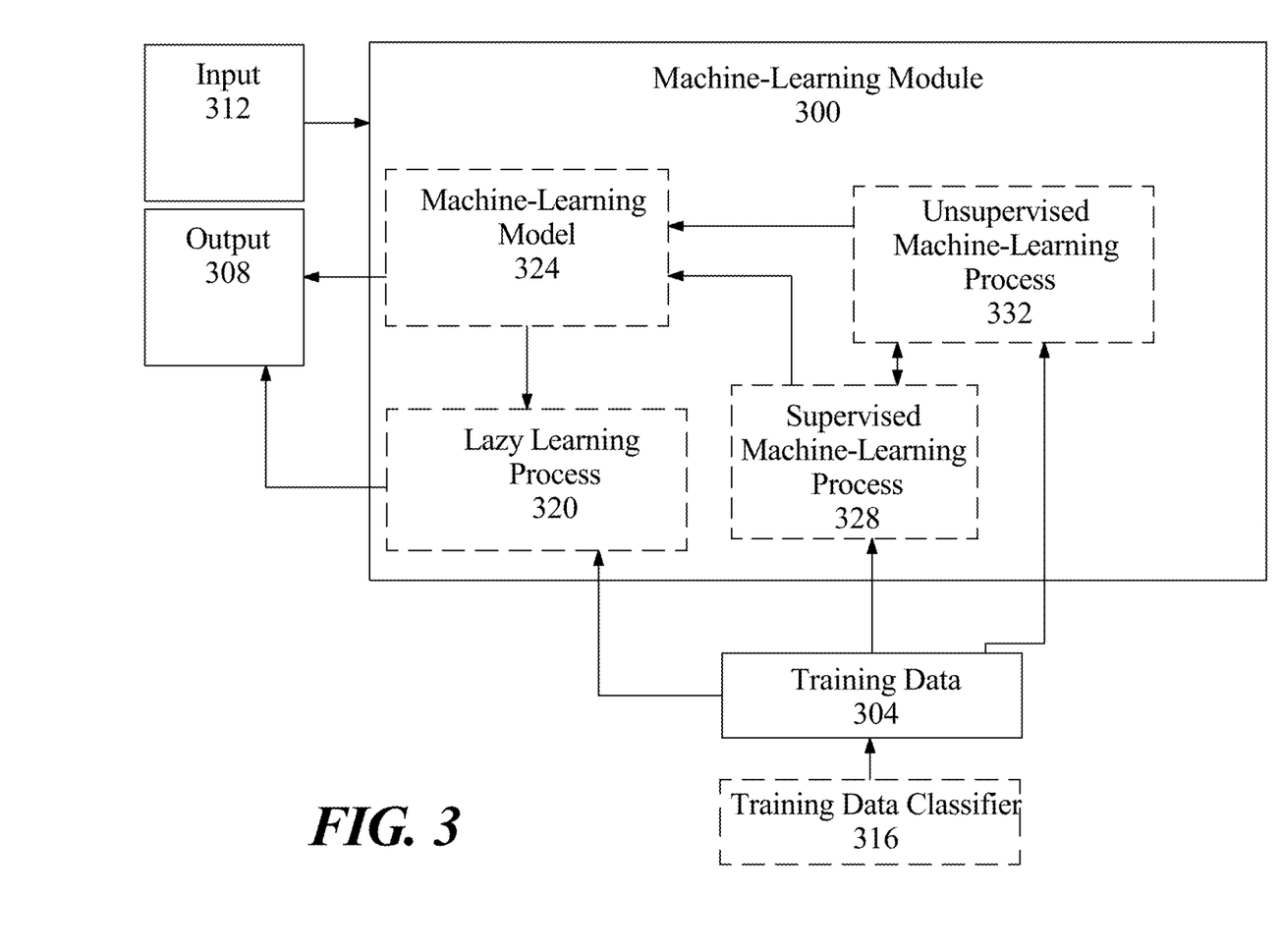
FIG. 3 is a block diagram illustrating an exemplary embodiment of a machine-learning system in accordance with one or more aspect of the present disclosure.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include first training set, second training set, third training set, among a plurality of other data entries, each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns updated by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example, a first training set m input to marker machine learning model to output the marker classifier.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm, defined as a processes whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to specific autoimmune disorders, or autoimmune disorder types, where an autoimmune disorder type may be classified based on the location of the autoimmune disorder in the body.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include first training set as described above as inputs, marker classifier as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be updated to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 3, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 304.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 4:
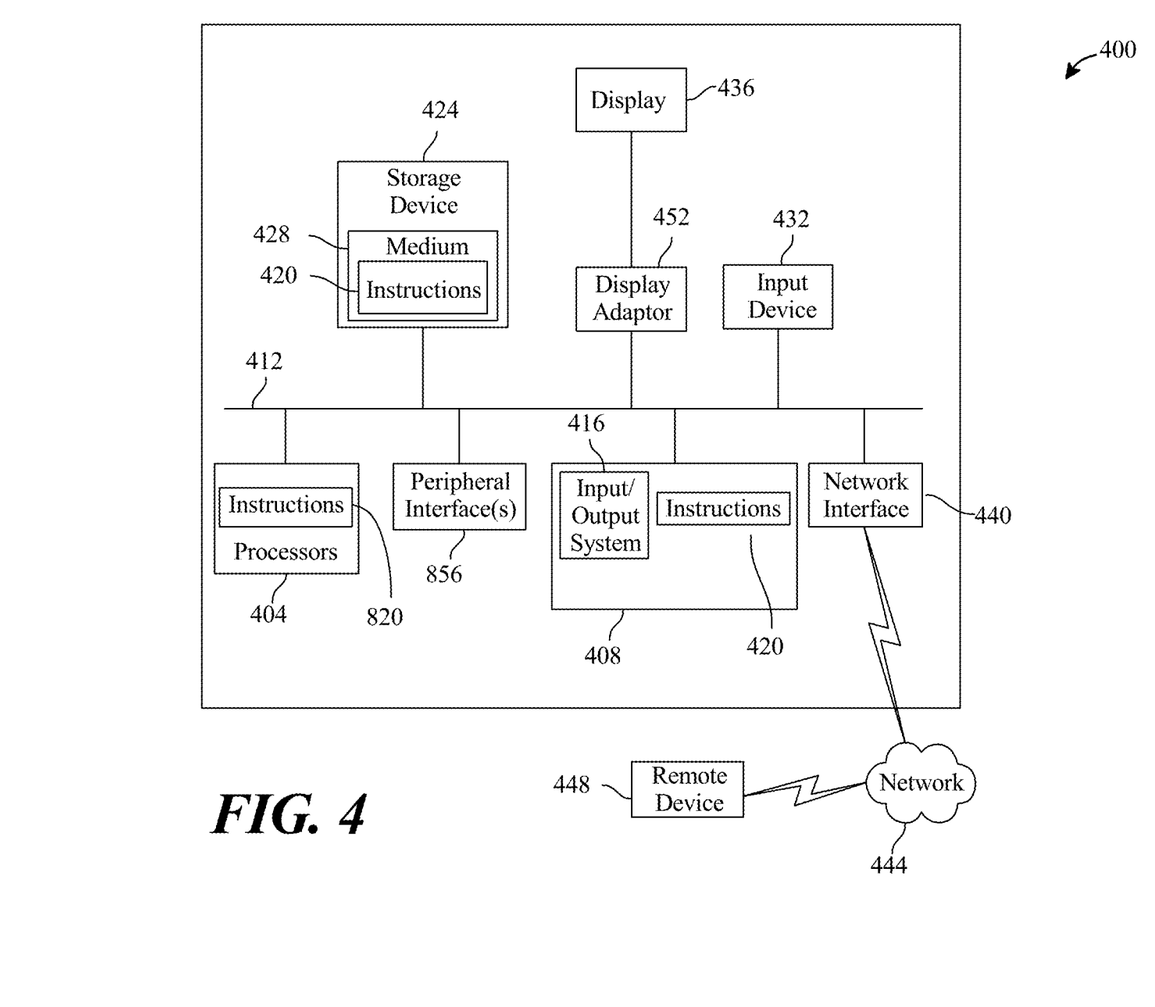
FIG. 4 is a block diagram of a computing system that can be used to implement any one or more of the methodologies disclosed herein and any one or more portions thereof.

FIG. 4 shows a diagrammatic representation of one embodiment of a computing device in the exemplary form of a computer system 400 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 400 includes a processor 404 and a memory 408 that communicate with each other, and with other components, via a bus 412. Bus 412 may include any of several types of bus structures including, but not limited to, a memory bus, a memory controller, a peripheral bus, a local bus, and any combinations thereof, using any of a variety of bus architectures.

Processor 404 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 404 may be organized according to Von Neumann and/or Harvard architecture as a non-limiting example. Processor 404 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 408 may include various components (e.g., machine-readable media) including, but not limited to, a random-access memory component, a read only component, and any combinations thereof. In one example, a basic input/output system 416 (BIOS), including basic routines that help to transfer information between elements within computer system 400, such as during start-up, may be stored in memory 408. Memory 408 may also include (e.g., stored on one or more machine-readable media) instructions (e.g., software) 420 embodying any one or more of the aspects and/or methodologies of the present disclosure. In another example, memory 408 may further include any number of program modules including, but not limited to, an operating system, one or more application programs, other program modules, program data, and any combinations thereof.

Computer system 400 may also include a storage device 424. Examples of a storage device (e.g., storage device 424)

include, but are not limited to, a hard disk drive, a magnetic disk drive, an optical disc drive in combination with an optical medium, a solid-state memory device, and any combinations thereof. Storage device 424 may be connected to bus 412 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 424 (or one or more components thereof) may be removably interfaced with computer system 400 (e.g., via an external port connector (not shown)). Particularly, storage device 424 and an associated machine-readable medium 428 may provide nonvolatile and/or volatile storage of machine-readable instructions, data structures, program modules, and/or other data for computer system 400. In one example, software 420 may reside, completely or partially, within machine-readable medium 428. In another example, software 420 may reside, completely or partially, within processor 404.

Computer system 400 may also include an input device 432. In one example, a user of computer system 400 may enter commands and/or other information into computer system 400 via input device 432. Examples of an input device 432 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 432 may be interfaced to bus 412 via any of a variety of interfaces (not shown) including, but not limited to, a serial interface, a parallel interface, a game port, a USB interface, a FIREWIRE interface, a direct interface to bus 412, and any combinations thereof. Input device 432 may include a touch screen interface that may be a part of or separate from display 436, discussed further below. Input device 432 may be utilized as a user selection device for selecting one or more graphical representations in a graphical interface as described above.

A user may also input commands and/or other information to computer system 400 via storage device 424 (e.g., a removable disk drive, a flash drive, etc.) and/or network interface device 440. A network interface device, such as network interface device 440, may be utilized for connecting computer system 400 to one or more of a variety of networks, such as network 444, and one or more remote devices 448 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 444, may employ a wired and/or a wireless mode of communication. In general, any network topology may be used. Information (e.g., data, software 420, etc.) may be communicated to and/or from computer system 400 via network interface device 440.

Computer system 400 may further include a video display adapter 452 for communicating a displayable image to a display device, such as display device 436. Examples of a display device include, but are not limited to, a liquid crystal display (LCD), a cathode ray tube (CRT), a plasma display, a light emitting diode (LED) display, and any combinations thereof. Display adapter 452 and display device 436 may be utilized in combination with processor 404 to provide graphical representations of aspects of the present disclosure. In addition to a display device, computer system 400 may include one or more other peripheral output devices including, but not limited to, an audio speaker, a printer, and any combinations thereof. Such peripheral output devices may be connected to bus 412 via a peripheral interface 456. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, apparatus, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for assessing a readiness of a medical entity to provide pediatric care, the apparatus comprising:
   at least a processor; and
   a memory communicatively connected to the at least a processor, the memory containing
     instructions configuring the at least a processor to:
     receive a pediatric patient profile of a patient;
     retrieve a current expertise status of a plurality of medical entities;
     obtain an optimal expertise criterion;
     identify a readiness score at various times of the day of each medical entity of the plurality of medical entities for patient care as a function of the pediatric patient profile, the current expertise status, and the optimal expertise criterion, wherein generating the readiness score comprises:
       receiving, by the processor, expertise training data, wherein the expertise training data comprises a plurality of current expertise statuses correlated with the readiness score;
       iteratively training by the processor, a readiness machine-learning model as a function of the expertise training data; and
       generating, by the processor, the readiness score as a function of the readiness machine-learning model; and determine a competency adjustment as a function of the readiness score and a preconfigured threshold when the readiness score is outside of the preconfigured threshold, wherein the preconfigured threshold includes a minimum readiness score necessary for the medical entity to care for the patient and the competency adjustment comprises at least one recommended action for the medical entity to increase the readiness score and determining the competency adjustment comprises:
   receiving, by the processor, competency training data, wherein the competency training data comprises the readiness score and the preconfigured threshold;
   training, by the processor, a competency machine-learning model as a function of the competency training data;
   determining, by the processor, the competency adjustment as a function of the competency machine-learning model;
   updating, by the processor, the competency training data as a function of the readiness score and the competency adjustment;
   retraining, by the processor, the competency machine-learning model as a function of the updated competency training data; and
  generate a recommendation score for each competency adjustment assigned to each medical entity of the plurality of medical entities as a function of the readiness score.

2. The apparatus of claim 1, wherein the competency adjustment comprises transferring the patient to a second medical entity if the readiness score exceeds the preconfigured threshold by a maximum magnitude.

3. The apparatus of claim 1, wherein the readiness score indicates that the medical entity needs a medical instrument to provide proper medical care to the patient.

4. The apparatus of claim 3, wherein the competency adjustment comprises contacting a second medical entity to acquire the medical instrument.

5. The apparatus of claim 1, wherein the competency adjustment comprises a certification program for training the medical entity.

6. The apparatus of claim 1, wherein the pediatric patient profile comprises a health condition of the pediatric patient.

7. The apparatus of claim 1, wherein the current expertise status includes a condition of an emergency medical services (EMS) transport.

8. The apparatus of claim 1, wherein the competency adjustment comprises a treatment protocol.

9. The apparatus of claim 1, wherein the current expertise status comprises a medical equipment inventory.

10. The apparatus of claim 1, wherein the medical entity comprises a medical professional.

11. The apparatus of claim 10, wherein the medical professional comprises a respiratory therapist (RT).

12. A method for assessing a readiness of a medical entity to provide pediatric care, the method comprising:
  receiving, by a processor, a pediatric patient profile of a patient;
  retrieving, by the processor, a current expertise status of a plurality of medical entities;
  obtain an optimal expertise criterion;
  identifying, by the processor, a readiness score at various times of the day of each medical entity of the plurality of medical entities for treating the patient as a function of the pediatric patient profile, the current expertise status, and the optimal expertise criterion, wherein generating the readiness score comprises:
   receiving, by the processor, expertise training data, wherein the expertise training data comprises a plurality of current expertise statuses correlated with the readiness score;
   iteratively training by the processor, a readiness machine-learning model as a function of the expertise training data; and
   generating, by the processor, the readiness score as a function of the readiness machine-learning model; and
  determining, by the processor, a competency adjustment as a function of the readiness score and a preconfigured threshold when the readiness score is outside of the preconfigured threshold, wherein the preconfigured threshold includes a minimum readiness score necessary for the medical entity to care for the patient and the competency adjustment comprises at least one recommended action for the medical entity to increase the readiness score and determining the competency adjustment comprises:
   receiving, by the processor, competency training data, wherein the competency training data comprises the readiness score and the preconfigured threshold;
   training, by the processor, a competency machine-learning model as a function of the competency training data;
   determining, by the processor, the competency adjustment as a function of the competency machine-learning model;
   updating, by the processor, the competency training data as a function of the readiness score and the competency adjustment;
   retraining, by the processor, the competency machine-learning model as a function of the updated competency training data; and
  generating, by the processor, a recommendation score for each competency adjustment assigned to each medical entity of the plurality of medical entities as a function of the readiness score.

13. The method of claim 11, wherein the competency adjustment comprises transferring the patient to a second medical entity if the quantity exceeds the preconfigured threshold by a maximum magnitude.

14. The method of claim 12, wherein the readiness score indicates that the medical entity needs a medical instrument to provide proper medical care to the patient.

15. The method of claim 14, wherein the competency adjustment comprises contacting a second medical entity to acquire the medical instrument.

16. The method of claim 12, wherein the current expertise status includes a condition of an emergency medical services (EMS) transport.

\* \* \* \* \*